United States Patent
Miyamoto

(12) 
(10) Patent No.: US 6,491,659 B1
(45) Date of Patent: Dec. 10, 2002

(54) LIQUID FLOW RATE CONTROLLER

(76) Inventor: Isshin Miyamoto, Fukuoka (JP)

( * ) Notice: Subject to any disclaimer, the term of this patent is extended or adjusted under 35 U.S.C. 154(b) by 0 days.

(21) Appl. No.: 09/517,816

(22) Filed: Mar. 2, 2000

(51) Int. Cl.$^7$ ................................................ A61M 1/00
(52) U.S. Cl. ...................................................... 604/30
(58) Field of Search ............................. 604/30, 65, 66, 604/67, 31, 131, 246, 256, 253, 250

(56) References Cited

U.S. PATENT DOCUMENTS

| | | | | |
|---|---|---|---|---|
| 3,601,124 A | * | 8/1971 | Petree | ........................ 137/486 |
| D416,999 S | | 11/1999 | Miyamoto | |

FOREIGN PATENT DOCUMENTS

JP            08317974        12/1996

* cited by examiner

Primary Examiner—Anhtuan T. Nguyen
Assistant Examiner—Ann Y Yam
(74) Attorney, Agent, or Firm—John V. Stewart

(57) ABSTRACT

A liquid flow rate detector and controller having a microprocessor that senses the rate of drops falling in a monitoring balloon on a fluid tube. A light emitter/detector diode pair detects drops as they fall in the balloon, which are timed by the microprocessor. The device has first and second switches manufactured in a single small unit made of thin laminates. Each switch comprises an electrode and a contact point, mutually facing across a gap in the layers. The lamina on at least one side of each switch is elastic. External force flexes the elastic layer, causing it to bend across the gap, causing the electrode and the contact point to touch. A fluid tube is inserted in a narrow channel between the first switch and a movable wedge. A stepper motor under control of the microprocessor moves the wedge to press the fluid tube against the first switch until the contacts close. This indicates that the fluid tube is completely flattened and closed. The microprocessor then retracts the wedge a predetermined distance from the closed point and monitors the rate of drops falling in the drip balloon. The movement of the wedge is precisely controlled by the microprocessor to achieve a desired drop rate. The second switch senses the presence of a fluid tube in the narrow channel to allow initialization of the process.

12 Claims, 5 Drawing Sheets

LIQUID FLOW RATE CONTROLLER

BACKGROUND OF THE INVENTION

1. Field of the Invention

This invention relates to liquid flow rate control devices, especially intravenous feeding control devices used in hospitals to control the flow rate of medical fluid.

2. Description of Prior Art

The feed rate of medical fluids during intravenous feeding is controlled by a device that automatically monitors and controls the flow rate in a feed tube. Such devices control the start time, feed rate, and stop time of the flow.

One method of flow control is to controllably squeeze the flexible feed tube with an electronically controlled clamp. However, it is very difficult to set the flow rate of a fluid precisely by clamping a flexible tube. The response of the flow to variations in constriction of the tube is extremely delicate. The clamp must be adjusted in steps of 0.001 mm, to provide adequate control. Medical fluid must be injected very slowly when a patient is in poor condition, and the flow must be controlled very precisely. For slow flow, the fluid tube must be flattened until it is barely open.

Prior apparatus for providing such delicate control is relatively complicated, large, and heavy. Prior devices are too heavy to hang on the medical tube without support, so attachment of the controller to a stand is required.

An example of a prior intravenous feeding control device having a wedge to squeeze a medical fluid tube for flow rate control is disclosed in the Patent Abstracts of Japan No. 1996-8317974.

SUMMARY OF THE INVENTION

The main objective of this invention is provision of a small, lightweight intravenous feeding control device capable of controlling the flow rate medical fluid very precisely. A further objective is an intravenous feeding control device that can be hung directly from a medical fluid feed tube without the need for attachment to a stand. Other objectives include simplicity of production, low expense, and high reliability.

The objectives are achieved in a liquid flow rate detector and controller having a microprocessor that senses the rate of drops falling in a monitoring balloon on a fluid tube. A light emitter/detector pair detects drops as they fall in the balloon, which are timed by the microprocessor. The device has first and second switches manufactured in a single small assembly made of thin laminates. Each switch comprises an electrode and a contact point, mutually facing across a gap in the layers. The lamina on at least one side of each switch is elastic. External force flexes the elastic layer, causing it to bend across the gap, causing the contact point to touch the electrode. A fluid tube is inserted in a narrow channel between the first switch and a movable wedge. A stepper motor under control of the microprocessor moves the wedge to press the fluid tube against the first switch until the contacts close. This indicates that the fluid tube is completely flattened and closed. The microprocessor then retracts the wedge a predetermined distance from the closed point and monitors the rate of drops falling in the drip balloon. The movement of the wedge is precisely controlled by the microprocessor to achieve a desired drop rate. The second switch senses the presence of a fluid tube in the narrow channel to allow initialization of the process.

BRIEF DESCRIPTION OF THE DRAWINGS

FIG. 3 is a front sectional view of FIG. 1 showing the wedge 6 clamping the outlet tube 5 against the limit switch 10a.

Figure 1:
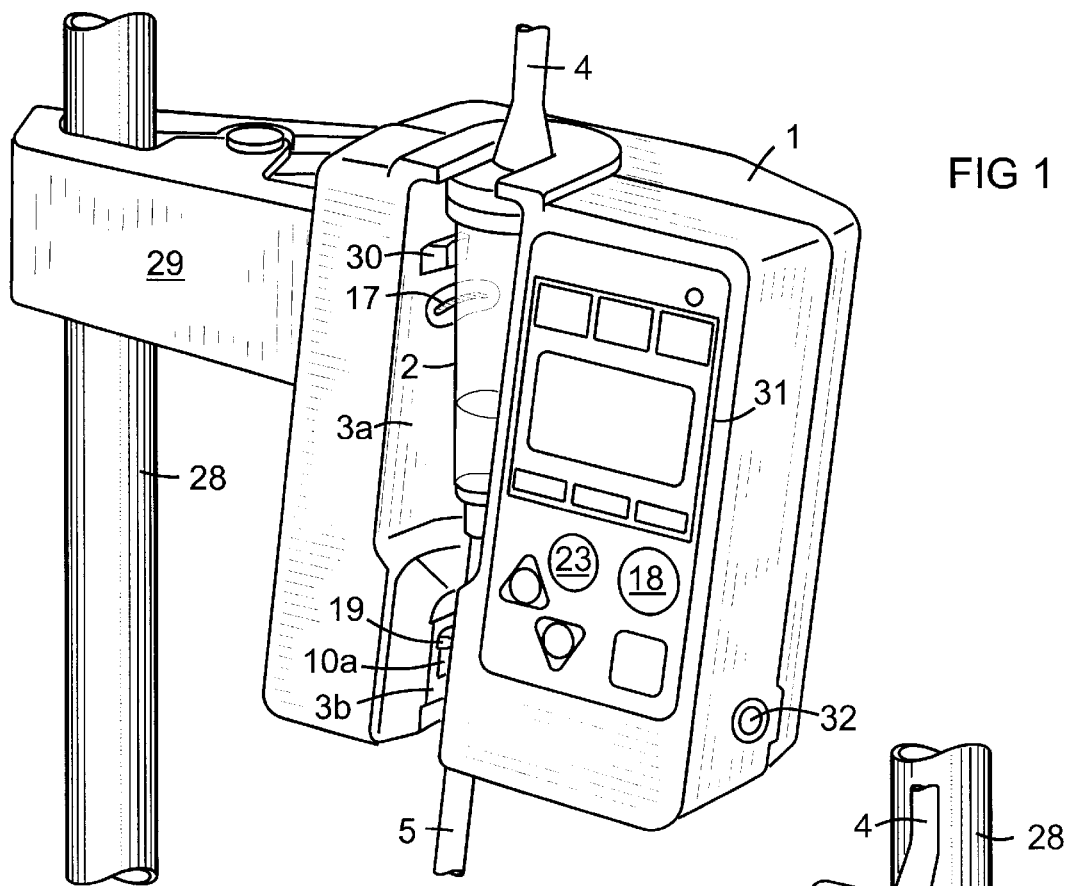
FIG. 1 is a front perspective view of a preferred embodiment of this invention installed on a stand in operation.

REFERENCE NUMBERS 1. case
2. Intravenous feeding drip balloon
3a. Storage hollow or wide portion of channel for intravenous feeding balloon
3b. Narrow portion of channel for outlet tube
4. inlet tube
5. Outlet tube
6. Wedge
7. Stepping motor
8. Switch assembly
9. Substrate
10a. First electrode (limit switch)
10b. Second electrode (tube presence detector switch)
11. Spacer
12a. First opening in spacer
12b. Second opening in spacer
13. Membrane
14a. First contact point
14b. Second contact point
15. Elasticity adjustment lamina
16. Light emitter
17. Light detector
18. Power switch
19. Lever
19a. Fulcrum of lever
19b. Button on lever
20. Microprocessor (CPU)
21. Input/output (I/O) interface
22. Battery
23. Start switch
24a. First air vent in the switch assembly
24b. Second air vent the switch assembly
25. Fluid drop
26. Force on limit switch caused by wedge
27. Force on tube presence detection switch from lever 19
28. Stand
29. Clip for mounting case on stand
30. Balloon retainer 31. Control Panel
32. Jack for A/C adapter plug

DESCRIPTION OF THE PREFERRED EMBODIMENTS

The invention is liquid flow rate controller designed for intravenous feeding. It has a case 1 with a channel that includes a wide portion 3a for holding a drip monitoring balloon 2. A fluid inlet tube 4 supplies the balloon, and an outlet tube 5 drains the balloon. A narrow portion 3b of the case channel holds the outlet tube.

A movable wedge 6 is mounted to press against the outlet tube 5. A stepper motor 7 drives and positions the wedge precisely under control of a microprocessor 20. A switch assembly 8 senses the condition of the outlet tube 5. The wedge and the switch assembly are mounted on opposite sides of the narrow portion 3b of the channel. The switch assembly has two pressure detection switches. The first switch or limit switch 10a is located opposite the wedge on the extension of the axis of the wedge. The limit switch closes when the wedge presses the outlet tube 5 against the limit switch sufficiently to close the outlet tube. This signals the microprocessor that the outlet tube has been closed by the wedge.

The second switch 10b is used for detecting the presence of a tube in the narrow portion 3b of the channel. This switch is spaced apart from the limit switch and is operated by a lever 19. The lever is fixed to the case 1 by an elastic fulcrum 19a. The lever extends partly into the narrow portion 3b of the channel, where it touches the outlet tube 5. A small button 19b protrudes from an intermediate point on lever 19 corresponding to the second switch 10b of the switch assembly 8. When a tube 5 is inserted in the narrow portion 3b of the channel, it pushes the lever aside, which presses the button 19b into the second switch, closing the switch. This signals the microprocessor that a tube is present in the narrow portion of the channel.

Figure 8:
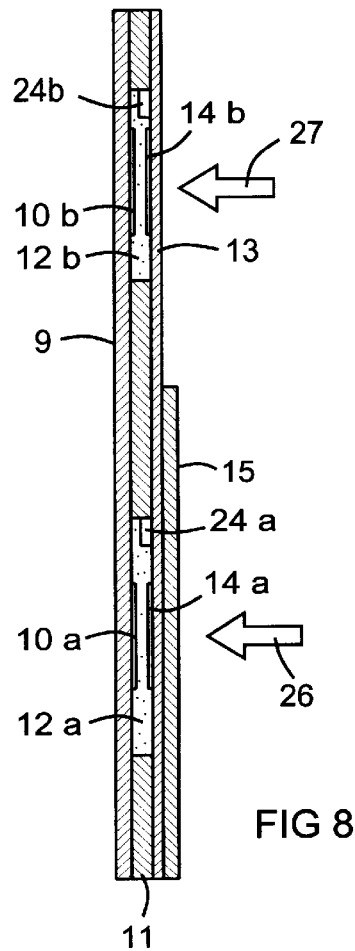
FIG. 8 is an enlarged sectional view of the limit switch assembly 8 taken along line 8—8 of FIG. 7.
Figure 7:
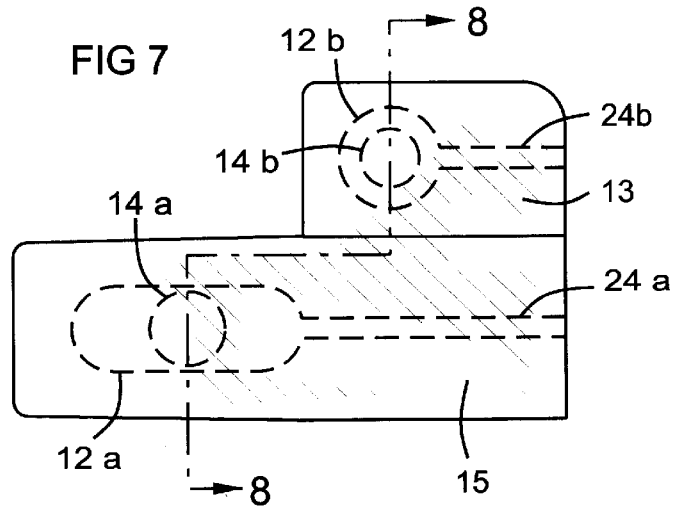
FIG. 7 is an enlarged right side view of the limit switch assembly 8.

FIGS. 7 and 8 are detail views of the switch assembly 8. Electrodes 10a and 10b are formed by printing a conductor material on substrate 9. A spacer 11 is adhered to substrate 9. Openings 12a and 12b are formed in spacer 11 over electrodes 10a and 10b respectively. A membrane 13 made of polyester film or the like is adhered over the spacer. Contact points 14a and 14b are formed by printing a carbon layer on the membrane 13. Contact points 14a and 14b face electrodes 10a and 10b respectively across openings 12a and 12b respectively. These elements form the first and second switches respectively for use as previously described. When the membrane 13 is depressed over an opening 12a or 12b, the membrane bends, causing the contact point 14a or 14b respectively to touch the electrode 10a or 10b respectively, closing the switch circuit and allowing current to flow. Each electrode is electrically connected to the microprocessor for input.

To provide a different sensitivity for each switch, an elasticity adjustment lamina 15 is adhered to membrane 13 over contact point 14a. It is made of polyurethane or other suitable material as later described. It can be made by a punching process from a larger polyurethane sheet. The sensitivity of the limit switch 14a can thus be set as desired in the design stage by the material and thickness of this adjustment lamina.

The air spaces enclosed in openings 12a and 12b of the spacer 11 are preferably vented by passages 24a and 24b in the spacer respectively. These vents 24a and 24b should be formed in a position that is difficult to enter by fluid even if fluid drips on the case. The vents 24a and 24b are formed by gaps in spacer 11 or by making openings in membrane sheet 13 or substrate 9. A designer can select vent locations that are difficult to enter by fluid. If the membrane 13 is soft, vents 24a and/or 24b are not required.

The elasticity adjustment lamina 15 bends when it is depressed over contact point 14a. This bends membrane 13, causing contact point 14a to approach electrode 10a. This causes air in opening 12a to escape through vent 24a. Contact point 14a touches electrode 10a when pressure on this switch becomes high enough. An electric current flows between contact point 14a and electrode 10a, and is communicated to the microprocessor by an electrical connection.

In the current model of this invention the sensitivity of the tube presence detection switch 10b is 0.2 Kgf (Kilogram force) and the sensitivity of the limit switch 10a is 1.3±0.2 Kgf.

Figure 9:
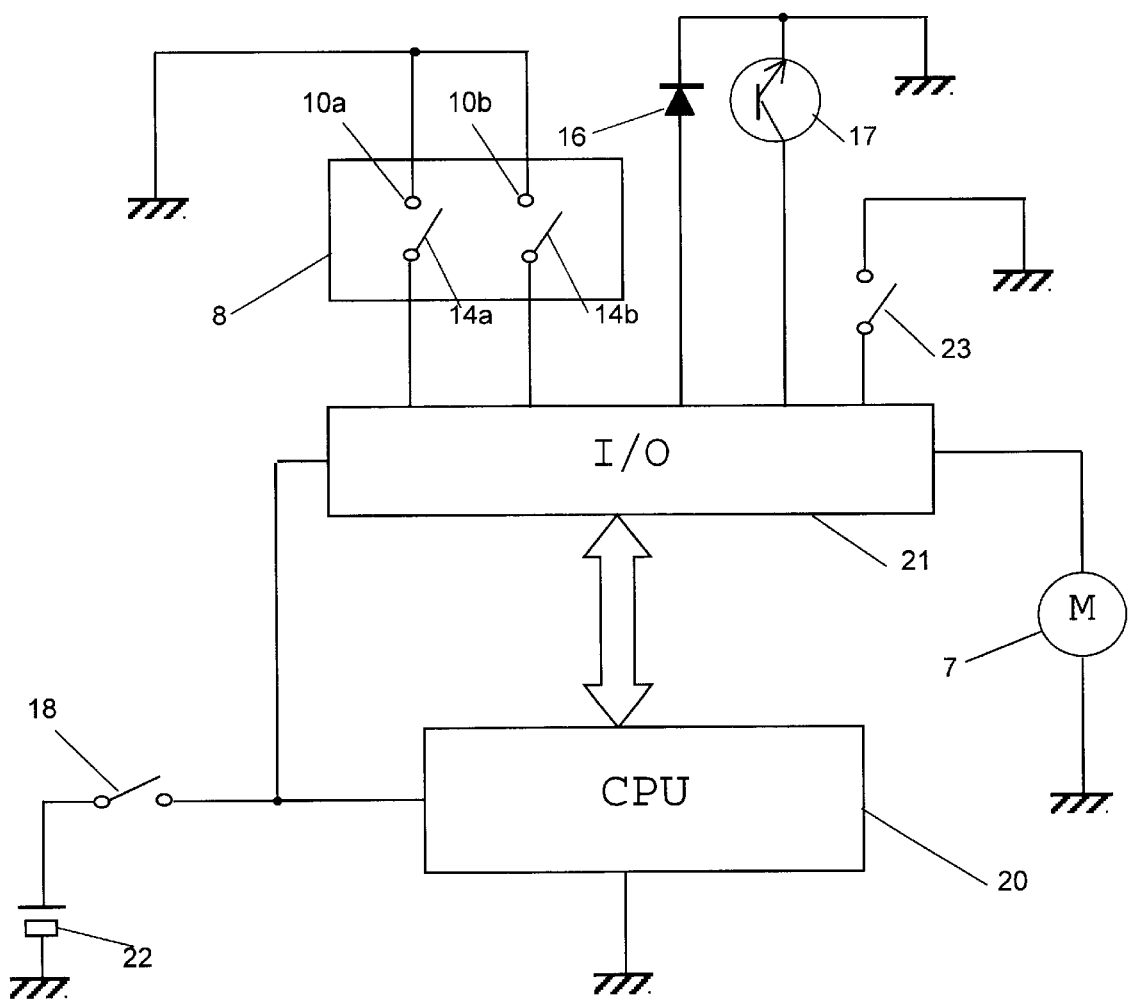
FIG. 9 is a schematic diagram of the electronic components
Figure 10:
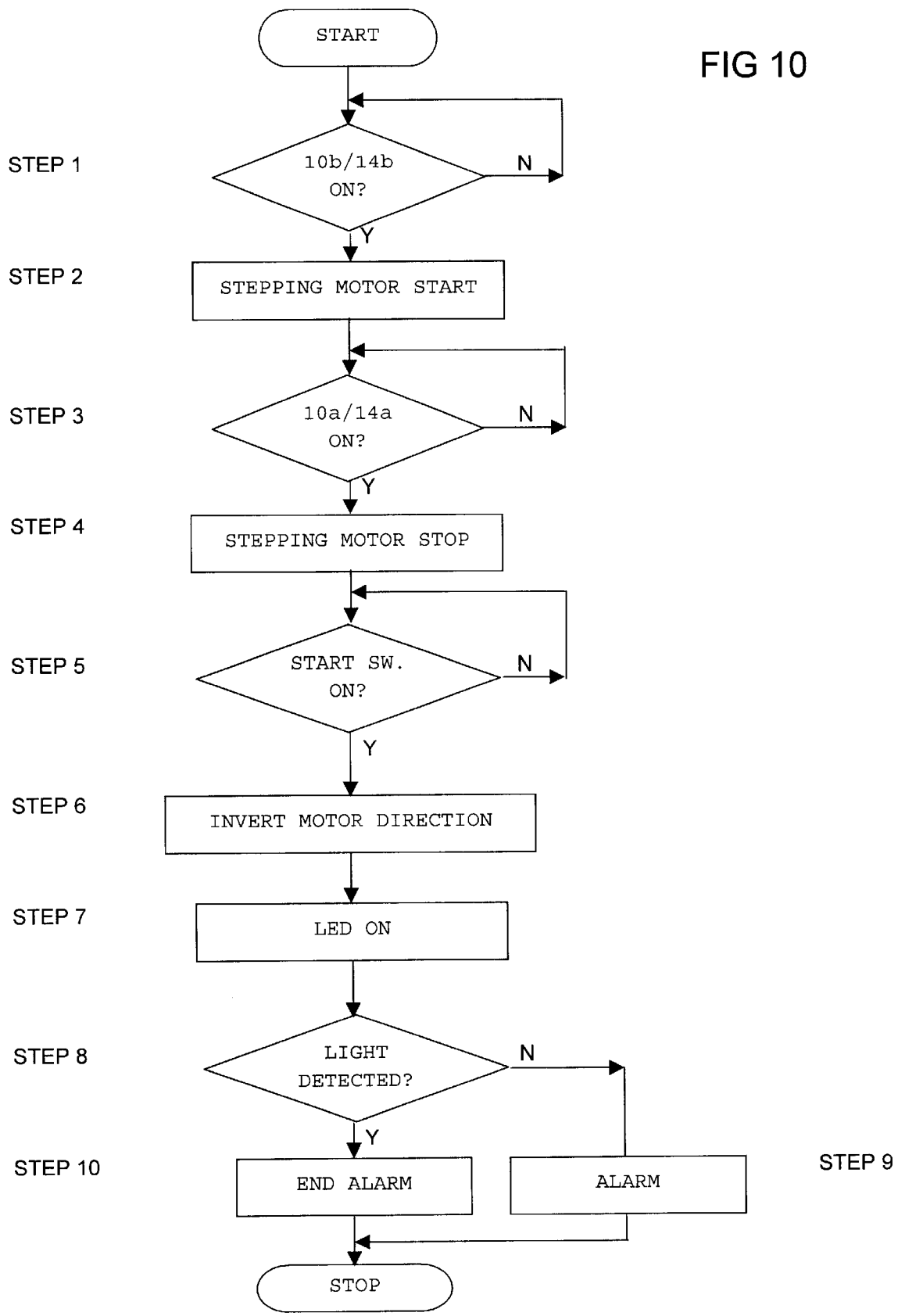
FIG. 10 is a flowchart of the control logic

Drops of liquid 25 falling in the drip-monitoring balloon 2 are detected by a light beam crossing the path of the drops. A light emitter 16, such as a light emission diode (LED), and a light detector 17, such as photo diode, are mounted on opposite sides of the wide portion 3a of the channel for this purpose. These elements are connected to the electronic circuit to receive electric power and for signaling to the CPU as shown in FIG. 9.

The preferred CPU 20 is an 8-bit type CPU that is marketed generally. Read-only memory, random access memory, and registers are included in the CPU 20 as known in the art. An input/output interface (I/O) 21 is connected to CPU 20 via a bus-line as known in the art. A 22 supplies electric power to the CPU 20 and I/O 21 through power switch 18. This is preferably a rechargeable battery. A DC jack 32 is provided on the case to receive current from external line voltage via an AC adapter for charging the battery as known in the art. A control panel 31 on the front of the case has input buttons and a display panel, which are electrically connected to the I/O 21 as known in the art. The stepping motor 7, limit switch 10a/14a, tube detection switch 10b/14b, light emitter 16, light detector 17, and an audible alarm are electrically connected to I/O 21.

OPERATION

The intravenous liquid and the control device are prepared in advance of the injection. The medical fluid feed tube 4 is initially clamped as known in the art to prevent flow until ready. Intravenous drip balloon 2 is set into the wide portion 3a of the channel. Output tube 5 is set into the narrow portion 3b of the channel, where it pushes lever 19. Lever 19 closes the tube presence detection switch 10b/14b.

Power switch 18 is turned-on, and electric power is supplied to the electronic circuit. The CPU 20 recognizes the closed condition of the tube detection switch 10b/14b at step 1. This tells the CPU that a tube is installed in the narrow portion 3b of the channel.

Next, stepping motor 7 starts at step 2, and wedge 6 presses against medical fluid tube 5. This flattens the fluid tube 5 gradually, and presses it against the elasticity adjustment lamina 15. When elasticity adjustment lamina 15 receives a pressure of 1.3±0.2 Kg/f, contact point 14a and electrode 10a touch and the limit switch 10a/14a is closed. This tells the CPU that tube 5 is completely flattened at step 3, and the CPU stops the stepping motor 7 at step 4. The flow of medical fluid is completely stopped.

In this condition, a nurse punctures the vein of a patient with an intravenous needle on the end of tube 5, opens the clamp on tube 4 and operates the start switch 23. The CPU 20 recognizes that start switch 23 is operated at step 5. At step 6, the CPU 20 controls stepping motor 7 to reverse the direction of stepping motor 7 and retracts the wedge 6 until the wedge moves a predetermined distance from the point where contact point 14a and electrode 10a contacted each other. This partially relieves the constriction of tube 5, and fluid flows by gravity in a specified quantity, for example 200 cc/hour. The amount of retraction of wedge 6 is determined by settings input to the microprocessor via buttons on the control panel to give an appropriate flow rate for the needs of the patient.

At step 7 the CPU 20 drives LED 16, and at step 8 the CPU 20 monitors the output signal of light detector 17. Medical fluid drips from tube 4 in the intravenous feeding balloon 2. The light of LED 16 is interrupted by each drop of fluid, causing the output signal of light detector 17 to become a plus. The plus signal from the light detector 17, is monitored and timed by CPU 20. CPU 20 controls the pressure of wedge 6 on medical fluid tube 5 to adjust the plus signals to a predetermined frequency.

If a plus wave output signal is earlier or later than a predetermined value, the CPU 20 goes to step 9 and outputs an alarm signal. In this case, there is trouble in the intravenous feeding, so the device stops the intravenous feeding and waits for correction by an operator.

When the output signal pulse stops, the CPU 20 recognizes the end of intravenous feeding and goes to step 10. At step 10, CPU 20 outputs an alarm that indicates the end, and the CPU 20 ends its action.

Although a suggested material of the elasticity adjustment lamina 15 is polyurethane sheet, it can alternately be made of a thin sheet metal such as stainless steel or phosphorus bronze about 0.05 mm thick. This provides maximum durability for the elasticity adjustment lamina 15, since metal has higher hardness than polyurethane.

Mass production of the limit switch is easy and inexpensive, because both substrate 9 and membrane 13 can be made by a printing process, and spacer 11 and elasticity adjustment lamina 15 can be made by a punching process. The elasticity of elasticity adjustment lamina 15 can be easily designed by selecting the thickness and material of the sheet.

The limit switch of the intravenous feeding control unit of this invention is composed of very thin layers, making miniaturization possible. Therefore the intravenous feeding control unit of this invention is small and light enough to hang directly from a medical fluid tube with no other support. The switch assembly can be mounted where the medical fluid is difficult to enter to inside of the switch, because the switch is thin and small. Even if fluid is spilled, it will not reach the contacts of the switch because they are sealed in the assembly.

The elasticity of the elasticity adjustment lamina 15 is stabilizing. Accordingly, the limit switch is mechanically stabilizing. This allows delicate control of the flow quantity of medical fluid by delicate flattening of the medical fluid tube. Precision of about 0.001 mm is required to control the medical fluid by flattening.

Figure 2:
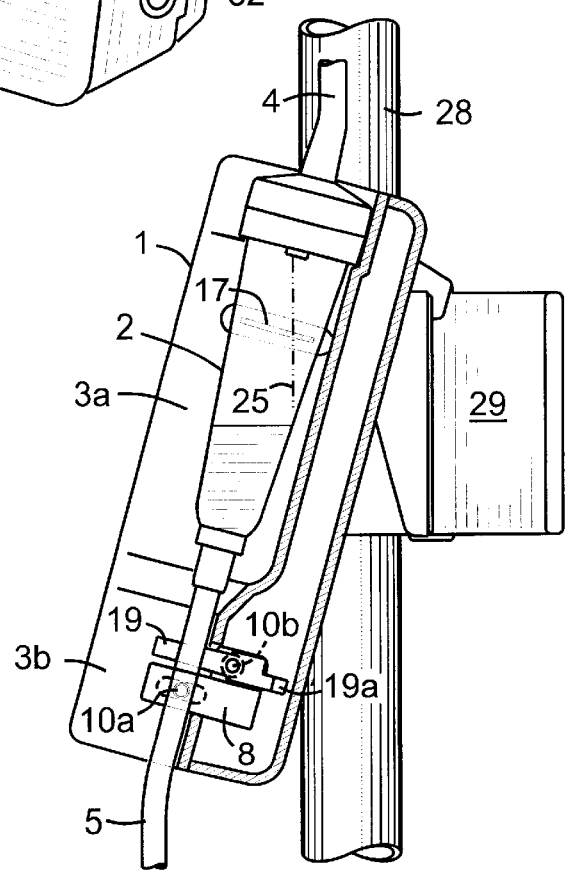
FIG. 2 is a side sectional view taken through the center of the channel 3a, 3b as viewed from the right side of FIG. 1.
Figure 3:
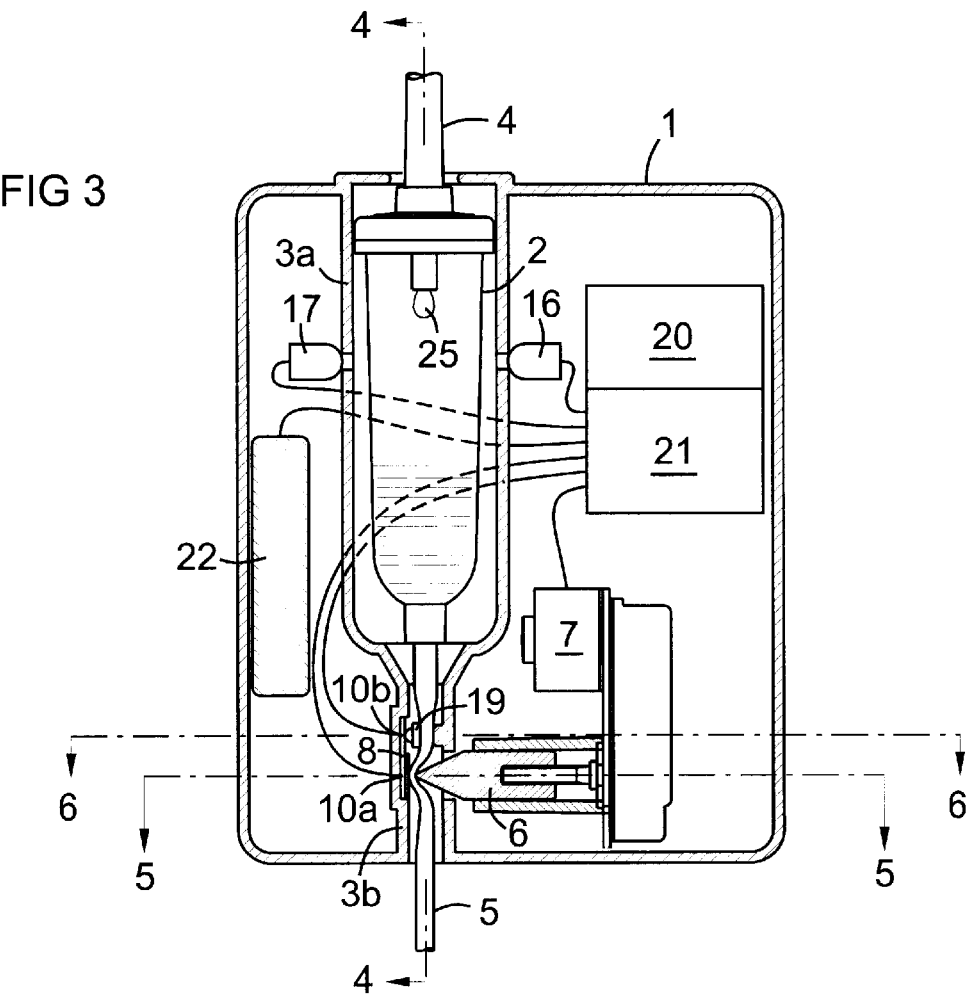
Figure 4:
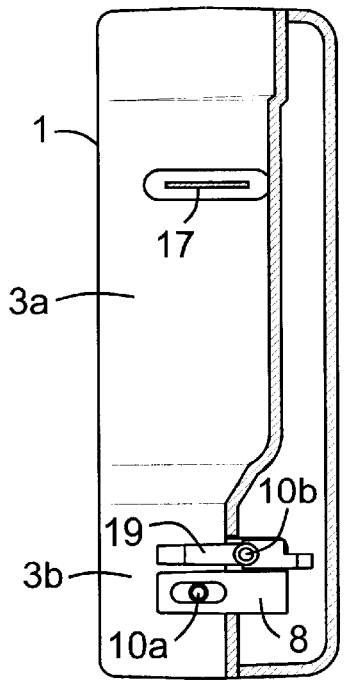
FIG. 4 is a side sectional view taken along line 4—4 of FIG. 3 without the drip balloon.
Figure 5:
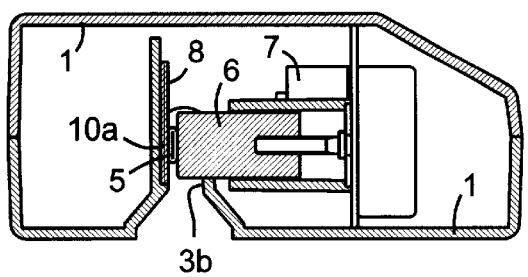
FIG. 5 is a top sectional view taken along line 5—5 of FIG. 3.
Figure 6:
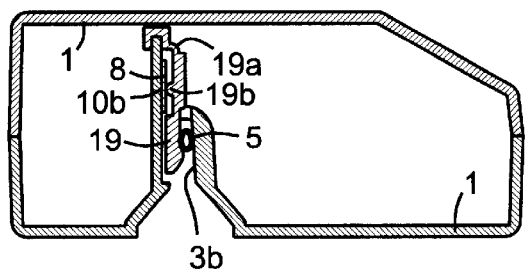
FIG. 6 is a top sectional view taken along line 6—6 of FIG. 3.

When the intravenous feeding control device is fixed on a stand at an angle of between 10 and 20 degrees, as in FIG. 2, the fluid 25 drips on the inner surface of he balloon 2 and not directly on the upper surface of the fluid. Therefore, drops do not splash back from the surface of the medical fluid and stick on the inner surface of the balloon 2. This avoids spurious interruption of the light beam.

The microprocessor preferably has logic that includes alarm functions for all abnormal situations and out-of-range conditions, such as low battery charge, and generates information on the display for prompting the user, tracking progress of operations, providing different modes of display, and providing information.

Although the present invention has been described herein with respect to preferred embodiments, it will be understood that the foregoing description is intended to be illustrative, not restrictive. Modifications of the present invention will occur to those skilled in the art. All such modifications that fall within the scope of the appended claims are intended to be within the scope and spirit of the present invention. Although this device is designed for intravenous fluid flow rate control, it may be used in other fluid flow control applications where a precise flow rate is needed or desired.

I claim:

1. An intravenous feeding control device comprising:
   a limit switch having a contact point and an electrode to detect a pressure applied to a medical fluid tube;
   a wedge that presses the medical fluid tube into the limit switch;
   drive means for moving the wedge to push and release the medical fluid tube;
   control means electrically connected to the limit switch and the drive means for controlling the drive means to close and open the medical fluid tube.

2. The intravenous feeding control device of claim 1 further comprising:
   a storage hollow in the front of intravenous feeding control device to receive an intravenous balloon.

3. The intravenous feeding control device of claim 2 wherein the storage hollow is elongated, and has an axis that is slanted between 10 and 20 degrees from a vertical path of fluid drops falling in the balloon.

4. An intravenous feeding control device of claim 1 comprising;
   a combination of light emission element and light detect element to detect a drop of medical fluid in an intravenous balloon.

5. A liquid flow rate controller comprising:
   a case;
   a channel in the case, having a narrow portion for holding a liquid transfer tube, and a wide portion for holding a liquid drip monitoring balloon attached to the tube;
   a light emitter and light detector on opposite sides of the wide portion of the channel for sensing drops of liquid falling in the balloon;
   a movable wedge;
   a limit switch;
   the wedge and limit switch on opposite sides of the narrow portion of the channel;
   drive means for moving the wedge toward the limit switch to compress the liquid tube against the limit switch;
   the light detector and limit switch electronically connected to a microprocessor for input thereto;
   the drive means connected to the microprocessor for control by the microprocessor;
   control logic in the microprocessor for moving the wedge toward the limit switch until the limit switch is closed, then reversing the wedge and making positional adjusatents thereto as required to achieve a given rate of detection of drops by the light detector.

6. The liquid flow rate controller of claim 5 further comprising:
   a tube presence detection switch in the case;

the tube presence detection switch electronically connected to the microprocessor for input thereto;

a lever projecting partly into the narrow portion of the channel apart from the wedge;

the lever contacting and closing the tube presence switch when a tube is inserted in the narrow portion of the channel;

whereby the microprocessor is informed of the presence of a tube in the narrow portion of the channel.

7. The liquid flow rate controller of claim 5 wherein the wide portion of the channel is elongated, and has an axis that is slanted between 10 and 20 degrees from vertical as defined by a path of drops of liquid falling in the balloon.

8. A liquid flow rate controller comprising:

a case having a channel with a narrow portion for accepting a fluid tube, and a wide portion for accepting a drip balloon;

a light emitter and a light detector on opposite sides of the wide channel portion, the light detector producing an electronic signal when a drop of fluid falls between the light emitter and detector;

a movable wedge protruding transversely into the narrow channel portion by a variable amount to press against the fluid tube with a respectively variable force;

a motor controlling the amount of protrusion of the wedge into the narrow channel portion;

a limit switch in the narrow channel portion opposite the wedge, activated by a threshold amount of lateral deflection of the fluid tube caused by the force exerted transversely on the tube by the wedge;

a tube presence detection switch in the narrow channel portion apart from the wedge, the tube presence detection switch activated by the presence of a fluid tube inserted in the narrow channel portion;

a control panel on the case, having input switches and a display panel;

an electronic logic device connected electronically to the control panel, limit switch, tube presence detection switch, motor, and light detector, the electronic logic device programmed to detect the signal rate from the light detector and to control the motor to achieve a selected signal rate from the light detector;

whereby a fluid tube having an in-line drip balloon can be placed in the channel and the rate of a fluid flowing through the tube is controlled as desired.

9. The liquid flow rate controller of claim 8, wherein the limit switch and tube presence detection switch are part of a switch assembly made by laminating layers of material, including at least a spacer sandwiched between a substrate and a membrane, the membrane being flexible, the spacer having at least first and second openings, within each of which an electrode is attached to the substrate and an opposed contact point is attached to the membrane, thus defining the limit switch and tube presence detection switch respectively, whereby the flexible membrane can be externally depressed at either of said switches, causing the respective contact point to touch the opposed electrode.

10. The switch assembly of claim 9, further comprising a flexibility adjustment layer bonded externally to the membrane over one of said switches to increase the pressure required to activate said one of said switches.

11. The liquid flow rate controller of claim 8, further comprising a lever extending across part of the narrow channel portion, the lever being pushed aside when a tube is inserted in the narrow channel portion, and the lever depressing the second limit switch when a tube is inserted in the narrow channel portion.

12. The liquid flow rate controller of claim 8 wherein the wide portion of the channel is elongated, and has an axis that is slanted between 10 and 20 degrees from vertical as defined by a path of drops of liquid falling in the balloon.

* * * * *